(12) United States Patent
Eicken et al.

(10) Patent No.: US 6,503,932 B2
(45) Date of Patent: Jan. 7, 2003

(54) FUNGICIDAL MIXTURES BASED ON AMIDE COMPOUNDS

(75) Inventors: Karl Eicken, Wachenheim (DE); Eberhard Ammermann, Heppenheim (DE); Reinhard Stierl, Mutterstadt (DE); Gisela Lorenz, Hambach (DE); Siegfried Strathmann, Limburgerhof (DE); Maria Scherer, Landau (DE); Klaus Schelberger, Gönnheim (DE); Manfred Hampel, Neustadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/012,347

(22) Filed: Dec. 12, 2001

(65) Prior Publication Data

US 2002/0123515 A1 Sep. 5, 2002

(30) Foreign Application Priority Data

Dec. 14, 2000 (DE) .......................... 100 62 326

(51) Int. Cl.⁷ .................. A01N 43/40; A01N 43/12; A01N 43/26
(52) U.S. Cl. .................. 514/355; 514/344; 514/345; 514/348; 514/349; 514/462
(58) Field of Search .................. 514/355, 462, 514/344, 345, 348, 349

(56) References Cited

U.S. PATENT DOCUMENTS

| | | | |
|---|---|---|---|
| 4,851,405 A | 7/1989 | Kramer | 514/212 |
| 5,330,995 A | 7/1994 | Eicken | 514/355 |
| 6,262,091 B1 | 7/2001 | Wagner et al. | 514/355 |

FOREIGN PATENT DOCUMENTS

| | | |
|---|---|---|
| AU | 740846 | 6/1999 |
| WO | WO 97/39628 | 10/1997 |
| WO | WO 99/27788 | 6/1999 |

*Primary Examiner*—Allen J. Robinson
(74) *Attorney, Agent, or Firm*—Keil & Weinkauf

(57) ABSTRACT

Fungicidal mixtures, comprising

A) an amide compound of the formula I

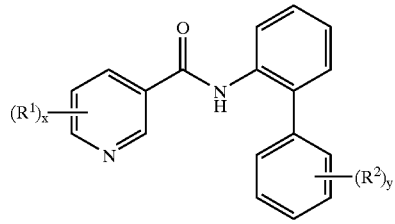

in which $R^1$, $R^2$ are identical or different and are halogen, nitro, cyano, $C_1$–$C_8$-alkyl, $C_2$–$C_8$-alkenyl, $C_2$–$C_8$-alkynyl, $C_1$–$C_8$-haloalkyl, $C_2$–$C_8$-haloalkenyl, $C_2$–$C_8$-haloalkynyl, $C_1$–$C_8$-alkoxy, $C_1$–$C_8$-haloalkoxy, $C_1$–$C_8$-haloalkylthio, $C_1$–$C_8$-alkylsulfinyl or $C_1$–$C_8$-alkylsulfonyl;

x is 1, 2, 3 or 4;

y is 1, 2, 3, 4 or 5;

and

B) the amino compound of the formula II

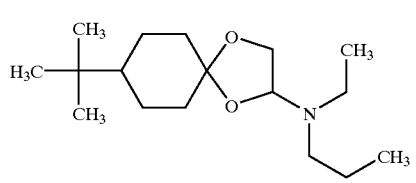

in a synergistically effective amount, methods for controlling harmful fungi using mixtures of the compounds I and II and the use of the compounds I and II for preparing such mixtures are described.

7 Claims, No Drawings

FUNGICIDAL MIXTURES BASED ON AMIDE COMPOUNDS

The present invention relates to fungicidal mixtures, comprising

A) an amide compound of the formula I

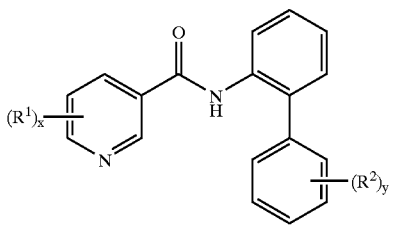

in which

R$^1$, R$^2$ are identical or different and are halogen, nitro, cyano, C$_1$–C$_8$-alkyl, C$_2$–C$_8$-alkenyl, C$_2$–C$_8$-alkynyl, C$_1$–C$_8$-haloalkyl, C$_2$–C$_8$-haloalkenyl, C$_2$–C$_8$-haloalkynyl, C$_1$–C$_8$-alkoxy, C$_1$–C$_8$-haloalkoxy, C$_1$–C$_8$-haloalkylthio, C$_1$–C$_8$-alkylsulfinyl or C$_1$–C$_8$-alkylsulfonyl;

x is 1, 2, 3 or 4;

y is 1, 2, 3, 4 or 5;

and

B) the amino compound of the formula II

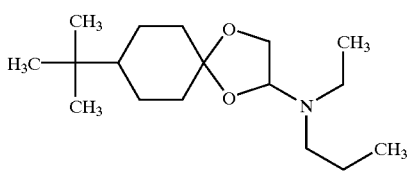

in a synergistically effective amount.

Moreover, the invention relates to methods for controlling harmful fungi using mixtures of the compounds I and II and to the use of the compounds I and II for preparing such mixtures.

The compounds of the formula I, their preparation and their action against harmful fungi have been disclosed in the literature (EP-A 545 099).

Also known is the compound II (common name: spiroxamin), its preparation and its action against pests (EP-A 281 842).

It is an object of the present invention to provide mixtures which have an improved activity against harmful fungi combined with a reduced total amount of active compounds applied (synergistic mixtures), with a view to reducing the application rates and improving the activity spectrum of the known compounds I and II.

We have found that this object is achieved by the mixtures defined at the outset. Moreover, we have found that applying the compounds I and the compounds II simultaneously, that is either together or separately, or applying the compounds I and the compounds II in succession provides better control of harmful fungi than is possible with the individual compounds alone.

The mixtures according to the invention act synergistically and are therefore particularly suitable for controlling harmful fungi and in particular powdery mildew fungi in cereals, vegetables, fruits, ornamental plants and grapevines.

The formula I represents in particular compounds in which R$^1$ is located in the 2-position and R$^2$ is located in the 4-position (formula I.1):

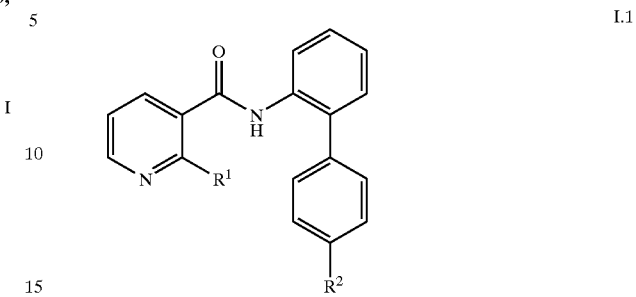

Particular preference is given to compounds of the formula I.1 in which the combination of the substituents corresponds to one row of Table I below:

| No. | R$^1$ | R$^2$ |
|---|---|---|
| I-1 | F | F |
| I-2 | F | Cl |
| I-3 | F | Br |
| I-4 | Cl | F |
| I-5 | Cl | Cl |
| I-6 | Cl | Br |
| I-7 | CF$_3$ | F |
| I-8 | CF$_3$ | Cl |
| I-9 | CF$_3$ | Br |
| I-10 | CF$_2$H | F |
| I-11 | CF$_2$H | Cl |
| I-12 | CF$_2$H | Br |
| I-13 | CH$_3$ | F |
| I-14 | CH$_3$ | Cl |
| I-15 | CH$_3$ | Br |
| I-16 | OCH$_3$ | F |
| I-17 | OCH$_3$ | Cl |
| I-18 | OCH$_3$ | Br |
| I-19 | SCH$_3$ | F |
| I-20 | SCH$_3$ | Cl |
| I-21 | SCH$_3$ | Br |
| I-22 | S(O)CH$_3$ | F |
| I-23 | S(O)CH$_3$ | Cl |
| I-24 | S(O)CH$_3$ | Br |
| I-25 | SO$_2$CH$_3$ | F |
| I-26 | SO$_2$CH$_3$ | Cl |
| I-27 | SO$_2$CH$_3$ | Br |

Particular preference is given to the compounds I.1 in which R$^1$ is CF$_3$ or halogen and R$^2$ is halogen.

When preparing the mixtures, it is preferred to employ the pure active compounds I and II, to which further active compounds against harmful fungi or other pests, such as insects, arachnids or nematodes, or else herbicidal or growth-regulating active compounds or fertilizers can be admixed.

The mixtures of the compounds I and II, or the compounds I and II used simultaneously, jointly or separately, exhibit outstanding activity against a wide range of phytopathogenic fungi, in particular from the classes of the Ascomycetes, Basidiomycetes, Phycomycetes and Deuteromycetes. Some of them act systemically and can therefore be employed as foliar- and soil-acting fungicides.

They are especially important for controlling a large number of fungi in a variety of crop plants, such as cotton, vegetable species (e.g. cucumbers, beans, tomatoes, potatoes and cucurbits), barley, grass, oats, bananas, coffee, maize, fruit species, rice, rye, soya, grapevine, wheat, ornamentals, sugar cane, and a variety of seeds.

They are particularly suitable for controlling the following phytopathogenic fungi: *Blumeria graminis* (powdery mildew) in cereals, *Erysiphe cichoracearum* and *Sphaerotheca fuliginea* in cucurbits, *Podosphaera leucotricha* in apples, *Uncinula necator* in grapevines, Puccinia species in cereals, Rhizoctonia species in cotton, rice and lawns, Ustilago species in cereals and sugar cane, *Venturia inaequalis* (scab) in apples, Helminthosporium species in cereals, *Septoria nodorum* in wheat, *Botrytis cinera* (gray mold) in strawberries, vegetables, ornamentals and grapevines, *Cercospora arachidicola* in groundnuts, Pseudocercosporella herpotrichoides in wheat and barley, *Pyricularia oryzae* in rice, Phytophthora infestans in potatoes and tomatoes, *Plasmopara viticola* in grapevines, Pseudoperonospora species in hops and cucumbers, Alternaria species in vegetables and fruit, Mycosphaerella species in bananas and Fusarium and Verticillium species.

They can furthermore be employed in the protection of materials (for example the protection of wood), for example against *Paecilomyces variotii*.

The compounds I and II can be applied simultaneously, that is either together or separately, or successively, the sequence, in the case of separate application, generally not having any effect on the result of the control measures.

The compounds I and II are usually applied in a weight ratio of from 20:1 to 1:20, in particular from 10:1 to 1:10 and preferably from 5:1 to 1:5.

Depending on the kind of effect desired, the application rates of the mixtures according to the invention are, in particular in agricultural crop areas, from 0.01 to 8 kg/ha, preferably 0.1 to 5 kg/ha, in particular 0.5 to 3.0 kg/ha.

The application rates of the compounds I are from 0.01 to 2.5 kg/ha, preferably 0.05 to 2.5 kg/ha, in particular 0.05 to 1.0 kg/ha.

Correspondingly, in the case of the compound II, the application rates are from 0.01 to 10 kg/ha, preferably 0.05 to 5 kg/ha, in particular 0.1 to 2.0 kg/ha.

For seed treatment, the application rates of the mixture are generally from 0.001 to 250 g/kg of seed, preferably 0.01 to 100 g/kg, in particular 0.01 to 50 g/kg.

If phytopathogenic harmful fungi are to be controlled, the separate or joint application of the compounds I and II or of the mixtures of the compounds I and II is effected by spraying or dusting the seeds, the plants or the soils before or after sowing of the plants, or before or after plant emergence.

The fungicidal synergistic mixtures according to the invention or the compounds I and II can be formulated for example in the form of ready-to-spray solutions, powders and suspensions or in the form of highly concentrated aqueous, oily or other suspensions, dispersions, emulsions, oil dispersions, pastes, dusts, materials for broadcasting or granules, and applied by spraying, atomizing, dusting, broadcasting or watering. The use form depends on the intended purpose; in any case, it should ensure as fine and uniform as possible a distribution of the mixture according to the invention.

The formulations are prepared in a manner known per se, e.g. by adding solvents and/or carriers. The formulations are usually admixed with inert additives, such as emulsifiers and dispersants.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols, or of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl, octyl- or nonylphenol, alkylphenol or tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for broadcasting and dusts can be prepared by mixing or jointly grinding the compounds I or II or the mixture of the compounds I and II with a solid carrier.

Granules (e.g. coated granules, impregnated granules or homogeneous granules) are usually prepared by binding the active compound, or active compounds, to a solid carrier.

Fillers or solid carriers are, for example, mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials and fertilizers, such as ammonium sulfate, ammonium phosphate, ammonium nitrate, ureas, and products of vegetable origin, such as cereal meal, tree bark meal, wood meal and nutshell meal, cellulose powders or other solid carriers.

The formulations generally comprise from 0.1 to 95% by weight, preferably 0.5 to 90% by weight, of one of the compounds I or II or of the mixture of the compounds I and II. The active compounds are employed in a purity of from 90% to 100%, preferably 95% to 100% (according to NMR spectrum or HPLC).

The compounds I or II, the mixtures, or the corresponding formulations, are applied by treating the harmful fungi, their habitat, or the plants, seeds, soils, areas, materials or spaces to be kept free from them with a fungicidally effective amount of the mixture, or of the compounds I and II in the case of separate application.

Application can be effected before or after infection by the harmful fungi.

USE EXAMPLES

The synergistic activity of the mixtures according to the invention can be demonstrated by the following experiments:

The active compounds, separately or together, were formulated as a 10% strength emulsion in a mixture of 70% by weight of cyclohexanone, 20% by weight of Nekanil® LN (Lutensol® AP6, wetting agent having emulsifying and dispersing action based on ethoxylated alkylphenols) and 10% by weight of Emulphor® EL (Emulan® EL, emulsifier based on ethoxylated fatty alcohols) and correspondingly diluted with water to the desired concentration.

Evaluation was carried out by determining the infected leaf areas in percent. These percentages were converted into efficacies. The efficacy (W) was calculated as follows using Abbot's formula:

$$W=(1-\alpha)\cdot 100/\beta$$

α corresponds to the fungal infection of the treated plants in % and

β corresponds to the fungal infection of the untreated (control) plants in %

An efficacy of 0 means that the infection level of the treated plants corresponds to that of the untreated control plants; an efficacy of 100 means that the treated plants were not infected.

The expected efficacies of the mixtures of the active compounds were determined using Colby's formula [R. S. Colby, Weeds 15, 20–22 (1967)] and compared with the observed efficacies.

Colby's formula: $E = x + y - x \cdot y / 100$

E expected efficacy, expressed in % of the untreated control, when using the mixture of the active compounds A and B at the concentrations a and b x efficacy, expressed in % of the untreated control, when using active compound A at a concentration of a y efficacy, expressed in % of the untreated control, when using active compound B at a concentration of b.

The results for the activity against mildew of wheat are shown in the tables below

Use Example 1

Activity Against Mildew of Wheat

Leaves of potted wheat seedlings of the culivar "Kanzler" were sprayed to run off point with an aqueous preparation of active compound which had been prepared from a stock solution made of 10% of active compound, 85% of cyclohexanone and 5% of emulsifier, and 24 hours after the spray coating had dried on, dusted with spores of mildew of wheat (Blumeria graminis forma specialis tritici). The test plants were then placed in a greenhouse at 20–24° C. and 60–90% relative atmospheric humidity. After 7 days, the extent of the mildew development was determined visually in % infection of the total leaf area. The percentages were converted into efficacies.

TABLE A

Individual active compounds

| Example | Active compound | Concentration of active compound in the spray liquor [ppm] | Efficacy in % of the untreated control |
|---|---|---|---|
| 1 | Control (untreated) | (100% infection) | 0 |
| 2 | I-4 | 50 | 0 |
|   |     | 12.5 | 0 |
| 3 | I-5 | 50 | 30 |
|   |     | 12.5 | 0 |
| 4 | spiroxamine (II) | 3 | 20 |
|   |     | 1.5 | 0 |

TABLE B

Combinations according to the invention

| Example | Mixture of active compounds concentration mixing ratio | Observed efficacy | Calculated efficacy*) |
|---|---|---|---|
| 5 | I-4 + II<br>12.5 + 3 ppm<br>4:1 | 40 | 20 |
| 6 | I-4 + II<br>50 + 3 ppm<br>16:1 | 80 | 20 |
| 7 | I-4 + II<br>50 + 1.5 ppm<br>32:1 | 40 | 0 |
| 8 | I-5 + II | 80 | 20 |

TABLE B-continued

Combinations according to the invention

| Example | Mixture of active compounds concentration mixing ratio | Observed efficacy | Calculated efficacy*) |
|---|---|---|---|
|   | 12.5 + 3 ppm<br>4:1 | | |
| 9 | I-5 + II<br>50 + 3 ppm<br>16:1 | 100 | 44 |
| 10 | I-5 + II<br>50 + 1.5 ppm<br>32:1 | 100 | 30 |

*)calculated using Colby's formula

Use Example 2

Curative Activity Against Puccinia Recondita on Wheat (Wheat Leaf Rust)

Leaves of potted wheat seedlings of the cultivar "Kanzler" were dusted with spores of leaf rust (Puccinia recondita). Thereafter, the pots were kept for 24 hours in a chamber of high atmospheric humidity (90 to 95%) and at 20–22° C. During this time, the spores germinated and the germinal tubes penetrated into the leaf tissue. The next day, the infected plants were sprayed to run off point with an aqueous formulation of the active compound prepared from a stock solution made of 10% of active compound, 85% of cyclohexanone and 5% of emulsifier. After the spray coating had dried on, the test plants were cultivated in a greenhouse at 20–22° C. and 65–70% relative atmospheric humidity for 7 days. Thereafter, the extent of the rust fungus development on the leaves was determined. The percentages were converted into efficacies.

TABLE C

Individual active compounds

| Example | Active compound | Concentration of active compound in the spray liquor [ppm] | Efficacy in % of the untreated control |
|---|---|---|---|
| 11 | Kontrolle (untreated) | (100% infection) | 0 |
| 12 | I-4 | 200 | 0 |
|    |     | 50 | 0 |
|    |     | 12.5 | 0 |
| 13 | I-5 | 50 | 20 |
| 14 | spiroxamine (II) | 12.5 | 30 |
|    |     | 3 | 0 |
|    |     | 1.5 | 0 |

TABLE D

Combinations according to the invention

| Example | Mixture of active compounds concentration mixing ratio | Observed efficacy | Calculated efficacy*) |
|---|---|---|---|
| 15 | I-4 + II<br>50 + 12.5 ppm<br>4:1 | 90 | 30 |
| 16 | I-4 + II | 30 | 0 |

TABLE D-continued

Combinations according to the invention

| Example | Mixture of active compounds concentration mixing ratio | Observed efficacy | Calculated efficacy*) |
|---|---|---|---|
| 17 | 12.5 + 3 ppm<br>4:1<br>I-4 + II | 70 | 30 |
| 18 | 200 + 12.5 ppm<br>32:1<br>I-4 + II | 40 | 0 |
| 19 | 50 + 3 ppm<br>16:1<br>I-4 + II | 60 | 30 |
| 20 | 12.5 + 12.5 ppm<br>1:1<br>I-4 + II | 70 | 0 |
| 21 | 50 + 1.5 ppm<br>32:1<br>I-5 + II | 80 | 44 |
| 22 | 50 + 12.5 ppm<br>4:1<br>I-5 + II | 60 | 20 |
| 23 | 50 + 3 ppm<br>16:1<br>I-5 + II | 40 | 20 |
|  | 50 + 1.5 ppm<br>32:1 |  |  |

*)calculated using Colby's formula

The test results show that the observed efficacy in all mixing ratios is higher than the efficacy which had been calculated beforehand and using Colby's formula.

We claim:

1. A fungicidal mixture, comprising
A) an amide compound of the formula I

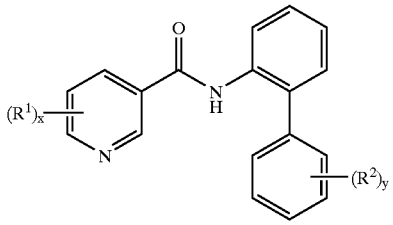

in which

R$^1$, R$^2$ are identical or different and are halogen, nitro, cyano, $C_1$–$C_8$-alkyl, $C_2$–$C_8$-alkenyl, $C_2$–$C_8$-alkynyl, $C_1$–$C_8$-haloalkyl, $C_2$–$C_8$-haloalkenyl, $C_2$–$C_8$-haloalkynyl, $C_1$–$C_8$-alkoxy, $C_1$–$C_8$-haloalkoxy, $C_1$–$C_8$-haloalkylthio, $C_1$–$C_8$-alkylsulfinyl or $C_1$–$C_8$-alkylsulfonyl;

x is 1, 2, 3 or 4;

y is 1, 2, 3, 4 or 5;

and

B) the amino compound of the formula II

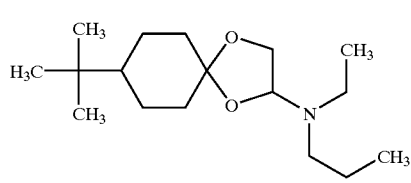

in a synergistically effective amount.

2. A fungicidal mixture as claimed in claim 1, wherein the weight ratio of compound I to compound II is from 20:1 to 1:20.

3. A method for controlling harmful fungi, which comprises treating the harmful fungi, their habitat or the plants, seeds, soils, areas, materials or spaces to be kept free from them with an effective amount of the composition of claim 1.

4. A method as claimed in claim 3, wherein a compound I and the compound II are applied simultaneously either together or separately, or successively.

5. A method as claimed in claim 3, wherein the compound I is applied in an amount of from 0.01 to 2.5 kg/ha.

6. A method as claimed in claim 3, wherein the compound II is applied in an amount of from 0.01 to 10 kg/ha.

7. A composition as claimed in claim 1 which is conditioned in two parts, one part comprising a compound of the formula I as set forth in claim 1 in a solid or liquid carrier and the other part comprising the compound of the formula II as set forth in claim 1 in a solid or liquid carrier.

* * * * *